United States Patent [19]

Seiler

[11] Patent Number: 5,059,239
[45] Date of Patent: Oct. 22, 1991

[54] SELECTIVE HERBICIDAL COMPOSITION
[75] Inventor: Alfred Seiler, Stein, Switzerland
[73] Assignee: Ciba-Geigy Corporation, Ardsley, N.Y.
[21] Appl. No.: 546,124
[22] Filed: Jun. 28, 1990
[30] Foreign Application Priority Data
  [CH] Switzerland .................. 2494/89
[51] Int. Cl.⁵ .................................... A01N 43/42
[52] U.S. Cl. .................................. 71/94; 71/107; 71/115
[58] Field of Search .................. 71/107, 115, 94
[56] References Cited
U.S. PATENT DOCUMENTS

| | | | |
|---|---|---|---|
| 3,598,859 | 8/1971 | Yates et al. | 71/100 |
| 3,761,508 | 9/1973 | Haddock | 71/111 |
| 4,047,928 | 9/1977 | Bond et al. | 71/107 |
| 4,902,340 | 2/1990 | Hubele | 71/94 |

Primary Examiner—Allen J. Robinson
Assistant Examiner—John D. Pak
Attorney, Agent, or Firm—Edward McC. Roberts

[57] ABSTRACT

A selective herbicidal composition for controlling grasses and weeds in crops of useful plants comprises a herbicidally effective amount of an N-benzoyl-phenylalanine herbicide and an effective amount of a herbicide antagonist of the formula:

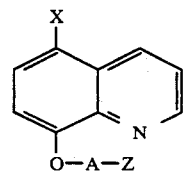

wherein X is hydrogen or halogen, A is —$CH_2$—, —$CH_2$—$CH_2$—, or —$CH(CH_3)$—, and Z is cyano, an amidoxime group, an acylamidoxime group, or a carboxylic acid group or derivative thereof, or A-Z taken together is a tetrahydrofuran-2-one group.

12 Claims, No Drawings

SELECTIVE HERBICIDAL COMPOSITION

The present invention relates to a selective herbicidal composition for controlling grasses and weeds in crops of useful plants, especially cereals, which comprises a herbicide and a safener which protects the useful plants, but not the weeds, from the phytotoxic action of the herbicide, and to the use of that composition or the combination of herbicide and safener in the control of weeds in crops of useful plants.

When herbicides are used, considerable damage may be caused to the cultivated plants depending on such factors as the concentration of herbicide and the mode of application, the species of cultivated plant, the nature of the soil and climatic conditions, for example period of exposure to light, temperature and rainfall. In particular, severe damage can be caused if, in the course of crop rotation, cultivated plants that are resistant to the herbicides are followed by other cultivated plants that have no or only insufficient resistance towards the herbicides.

Surprisingly, it has now been found that it is possible to protect cultivated plants against damage caused by the above-mentioned herbicides by treating the cultivated plants, parts of those plants or areas of land intended for the cultivation of the plants with a safener. The herbicidal action against weeds and weed grasses is not neutralised by this safener.

The selective herbicidal composition contains as active component a mixture comprising a) a herbicidally effective amount of an N-benzoyl-N-phenylalanine derivative of formula I

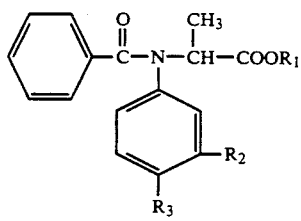

wherein $R_1$ is hydrogen or $C_1$-$C_4$alkyl and each of $R_2$ and $R_3$, independently of the other, is chlorine or fluorine, or the enantiomers thereof, and b) as safener, a herbicide-antagonistically effective amount of a quinoline derivative of formula II

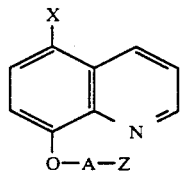

wherein X is hydrogen or a halogen,

A is one of the groups -$CH_2$-, -$CH_2$-$CH_2$-and -CH($CH_3$)- and

Z is cyano or amidoxime which may be acylated at the oxygen atom, a carboxy group or a salt thereof, a mercaptocarbonyl group or a salt thereof, a carboxylic acid ester group, a carboxylic acid thiol ester group, an unsubstituted or substituted carboxylic acid amide group, a cyclised, unsubstituted or substituted derivative of a carboxylic acid amide group or a carboxylic acid hydrazide group, or A and Z together are an unsubstituted or substituted tetrahydrofuran-2-one ring, including the acid addition salts and metal complexes thereof, together with inert adjuvants, such as carriers, solvents and wetting agents.

The compounds of formula I are known and are described, for example, in UK Patents 1 437 711 and 1 563 201.

Of the herbicides of formula I, in particular
N-benzoyl-N-(3-chloro-4-fluorophenyl)-DL-alanine,
N-benzoyl-N-(3-chloro-4-fluorophenyl)-DL-alanine methyl ester,
N-benzoyl-N-(3-chloro-4-fluorophenyl)-DL-ananine ethyl ester,
N-benzoyl-N-(3-chloro-4-fluorophenyl)-DL-alanine,
N-benzoyl-N-(3-chloro-4-fluorophenyl)-DL-alanine methyl ester,
N-benzoyl-N-(3-chloro-4-fluorophenyl)-D-alanine isopropyl ester,
N-benzoyl-N-(3-chloro-4-fluorophenyl)-L-alanine,
N-benzoyl-N-(3-chloro-4-fluorophenyl)-L-alanine methyl ester, are suitable for use in selective weed control.

They are prepared in a manner known per se by first reacting 3-chloro-4-fluoroaniline with a 2-bromopropionic acid derivative and then reacting the resulting 3-chloro-4-fluorophenylalanine derivative with benzoic acid chloride.

The compounds of formula II are known from the published European Patent Applications EP-A 86 750, EP-A 94 349 and EP 159290 and can be prepared in accordance with the methods described in those publications. In the definition of Z in the quinoline derivatives of formula II, amidoxime shall be understood as being the group —C($NH_2$)=N—OH. The amidoxime may be acylated at the oxygen atom. Suitable amidoximes acylated at the oxygen atom are those of the formula —C($NH_2$)=N—O—CO—E in which E is —$R^7$, —$OR^8$, —$SR^9$ or —$NR^{10}R^{11}$ wherein $R^7$ is $C_1$-$C_7$alkyl that is unsubstituted or substituted by halogen or by $C_1$-$C_4$alkoxy, $C_3$-$C_6$cycloalkyl, $C_2$-$C_4$alkenyl, phenyl that is unsubstituted or substituted by halogen, nitro or by $C_1$-$C_3$alkyl, benzyl that is unsubstituted or substituted by halogen, nitro or by $C_1$-$C_3$alkyl, or a 5-or 6-membered heterocyclic ring that contains one or two hetero atoms from the group, N, O and S and is unsubstituted or substituted by halogen, each of $R^8$, $R^9$ and $R^{10}$, independently of the others, is $C_1$-$C_8$alkyl that is unsubstituted or substituted by halogen, or is $C_2$-$C_4$alkenyl, $C_3$-$C_6$alkynyl, phenyl that is unsubstituted or substituted by halogen, $C_1$-$C_3$alkyl, $C_1$-$C_3$alkoxy, trifluoromethyl or by nitro, or benzyl that is unsubstituted or substituted by halogen or by nitro, $R^{11}$ is hydrogen, $C_1$-$C_8$alkyl or $C_1$-$C_3$alkoxy, or $R^{10}$ and $R^{11}$, together with the nitrogen atom to which they are bonded, are a 5-or 6-membered heterocycle that may contain a further hetero atom from the group N, O and S.

$R^7$ as a deterocycle may be a saturated, partially saturated or unsaturated heterocycle, for example thiophene, furan, tetrahydrofuran and pyrimidine.

Suitable heterocycles formed by $R^{10}$ and $R^{11}$ together with the nitrogen atom to which they are bonded are saturated, partially saturated or unsaturated heterocycles. Examples of such heterocycles are pyrrolidine, pyrroline, pyrrole, imidazolidine, imidazoline, imidazole, piperazine, pyridine, pyrimidine, pyrazine, thiazine, oxazole, thiazole and, especially, piperidine and morpholine.

Alkyl as a constituent of the acylated amidoxime Z is, within the limitation of the number of carbon atoms indicated, any straight-chain or any branched alkyl group.

$R^7$ as $C_3-C_6$cycloalkyl is cyclopropyl, cyclobutyl, cyclopentyl or cyclohexyl.

Of the $C_2-C_4$alkenyl and $C_3-C_6$alkylnyl groups as constituents of the acylated amidoxime Z, there may be mentioned in particular vinyl, allyl, 1-propenyl, methallyl and propargyl.

Z as a carboxylic acid ester group or a carboxylic acid thiol ester group is a corresponding acid radical that is esterified, for example, by an unsubstituted or substituted aliphatic radical or by an unsubstituted or substituted cycloaliphatic, aromatic or heterocyclic radical that may be bonded by way of an aliphatic radical.

Preferred as carboxylic acid ester radical is the radical $-COOR^{12}$ and, as carboxylic acid thiol ester radical, the radical $-COSR^{13}$, wherein $R^{12}$ and $R^{13}$ have the following meanings: an unsubstituted or substituted alkyl, alkenyl, alkynyl, cycloalkyl, phenyl or naphthyl radical or an unsubstituted or substituted heterocyclic radical. The radicals $-COOR^{12}$ and $-COSR^{13}$ also include the free acids, wherein $R^{12}$ and $R^{13}$ are hydrogen, and the salts thereof, wherein $R^{12}$ and $R^{13}$ are a cation. Suitable salt-forming agents are especially metals and organic nitrogen bases, especially quaternary ammonium bases. Metals suitable for salt formation are alkaline earth metals, such as magnesium or calcium, but especially the alkali metals, such as lithium and especially potassium and sodium. Also suitable as salt-forming agents are transition metals, for example iron, nickel, cobalt, copper, zinc, chromium or manganese. Examples of nitrogen bases suitable for salt formation are primary, secondary or tertiary, aliphatic and aromatic amines which may be hydroxylated at the hydrocarbon radical, such as methylamine, ethylamine, propylamine, isopropylamine, the four isomers of butylamine, dimethylamine, diethylamine, dipropylamine, diisopropylamine, di-n-butylamine, pyrrolidine, piperidine, morpholine, trimethylamine, triethylamine, tripropylamine, quinuclidine, pyridine, quinoline, isoquinoline and also methanolamine, ethanolamine, propanolamine, dimethanolamine, diethanolamine or trietholamine. Also suitable as organic nitrogen bases are quaternary ammonium bases. Examples of quaternary ammonium bases are tetraalkylammonium cations in which the alkyl radicals, independently of one another, are straight-chain or branched $C_1-C_6$alkyl groups, such as the tetramethylammonium cation, the tetraethylammonium cation or the trimethylethylammonium cation, and also the trimethylbenzylammonium cation, the triethylbenzylammonium cation and the trimethyl-2-hydroxyethylammonium cation. Especially preferred as salt-forming agents are the ammonium cation and trialkylammonium cations in which the alkyl radicals, independently of one another, are straight-chain or branched $C_1-C_6$alkyl groups, especially $C_1-C_2$alkyl groups, that are unsubstituted or substituted by a hydroxy group, for example the trimethylammonium cation, the triethylammonium cation and the tri(2-hydroxyethylene)-ammonium cation.

Z as a carboxylic acid amide group is a corresponding amide radical that may be unsubstituted or mono- or di-substituted at the nitrogen atom or in which the nitrogen atom is a constituent of an unsubstituted or substituted heterocyclic radical. There may be mentioned as substituents of the amide group, for example, an unsubstituted or substituted aliphatic radical that may be bonded by way of an oxygen atom, an unsubstituted or substituted cycloaliphatic, aromatic or heterocyclic radical that may be bonded by way of an aliphatic radical, or an unsubstituted or mono- or di-substituted amino group.

Preferred as carboxylic acid amide radical is the radical $-CONR^{14}R^{15}$ wherein $R^{14}$ is hydrogen, an unsubstituted or substituted alkyl, alkenyl, alkynyl, cycloalkyl, phenyl or naphthyl radical, an unsubstituted or substituted heterocyclic radical or an alkoxy radical, $R^{15}$ is hydrogen, amino, mono- or di-substituted amino or an unsubstituted or substituted alkyl, alkenyl, cycloalkyl or phenyl radical, $R^{14}$ and $R^{15}$, together with the nitrogen atom to which they are bonded, are an unsubstituted or substituted heterocyclic radical.

Suitable substituents of the organic radicals $R^{12}$, $R^{13}$, $R^{14}$ and $R^{15}$ are, for example, halogen, nitro, cyano, hydroxy, alkyl, haloalkyl, alkoxy, which may be interrupted by one or more oxygen atoms, alkylthio, haloalkoxy, hydroxyalkoxy, which may be interrupted by one or more oxygen atoms, hydroxyalkylthio, alkoxycarbonyl, amino, alkylamino, dialkylamino, hydroxyalkylamino, di-(hydroxyalkyl)-amino, aminoalkylamino, cycloalkyl, unsubstituted or substituted phenyl, unsubstituted or substituted phenoxy or an unsubstituted or substituted heterocyclic radical.

Heterocyclic radicals as constituents of the carboxylic acid ester radical, the carboxylic acid thiol ester radical and the carboxylic acid amide radical are preferably 5- or 6-membered, saturated or unsaturated, unsubstituted or substituted monocyclic heterocycles having from 1 to 3 hetero atoms from the group N, O and S, for example furan, tetrahydrofuran, tetrahydropyran, tetrahydropyrimidine, pyridine, piperidine, morpholine and imidazole.

Cycloalkyl radicals as constituents of the carboxylic acid ester radical, the carboxylic acid thiol ester radical and the carboxylic acid amide radical shall be understood as being especially those having from 3 to 8, especially from 3 to 6, carbon atoms.

Aliphatic, acyclic radicals present in the substituent Z as constituent of the carboxylic acid ester radical, the carboxylic acid thiol ester radical and the carboxylic acid amide radical may be straight-chained or branched and advantageously contain up to a maximum of 18 carbon atoms. A lower number of carbon atoms is often advantageous, especially in the case of substituents made up of a number of radicals.

Z as a cyclised derivative of a carboxylic acid amide group is especially an unsubstituted or substituted oxazolin-2-yl radical, preferably an unsubstituted oxazolin-2-yl radical.

A and Z may together form an unsubstituted or substituted tetrahydrofuran-2-one ring, the unsubstituted tetrahydrofuran-2-one ring being preferred, especially the unsubstituted tetrahydrofuran-2-on-3-yl ring.

In the compounds of formula II, halogen is fluorine, chlorine, bromine and iodine, especially chlorine, bromine and iodine.

Suitable salt-forming agents for acid addition salts are organic and inorganic acids. Examples of organic acids are acetic acid, trichloroacetic acid, oxalic acid, benzene-sulfonic acid and methanesulfonic acid. Examples of inorganic acids are hydrochloric acid, hydrobromic acid, hydriodic acid, sulfuric acid, phosphoric acid, phosphorous acid and nitric acid.

Suitable metal complex forming agents are, for example, elements of main groups III and IV, such as aluminium and tin, and of sub-groups I to VIII, for example manganese, iron, nickel, zinc, copper and silver. The sub-group elements of period IV are preferred.

If, in the compounds of formula I, A is —CH(CH₃)—, the radical Z contains an asymmetric carbon atom or A and Z together form a tetrahydrofuran-2-one ring, then those compounds are optical isomers. Within the scope of the present invention, such compounds of formula I shall be understood as being both the optically pure isomers and mixtures of the isomers. If, when one or more asymmetric carbon atoms are present, the structure is not given in detail, then the mixture of isomers is always to be understood.

Compounds of the following Table 1 are especially suitable for the use according to the invention.

TABLE 1

| No. | X | A | Z | physical constant |
|-----|---|---|---|-------------------|
| 1.1 | H | —CH₂— | —CN | m.p. 118–119° C. |
| 1.2 | H | —CH₂— | =N—OH, —NH₂ (C=NOH with NH₂) | m.p. 201–204° C. (decomp.) |
| 1.3 | H | —CH₂— | —CN | m.p. 114–116° C. |
| 1.4 | H | —CH₂— | =N—OH, —NH₂ | m.p. 209–210° C. (decomp.) |
| 1.5 | Cl | —CH₂— | =N—OH, —NH₂ | m.p. 203–205° C. (decomp.) |
| 1.6 | H | —CH₂— | =N—O—C(=O)—NH—C₃H₇-iso, —NH₂ | m.p. 136–138° C. |
| 1.7 | Cl | —CH₂— | —CN | m.p. 159–160° C. |
| 1.8 | H | —CH₂— | =N—O—C(=O)—CH₂Cl, —NH₂ | m.p. 129–130° C. |
| 1.9 | H | —CH₂— | =N—O—C(=O)—OCH₃, —NH₂ | m.p. 143–145° C. |
| 1.10 | H | —CH₂—CH₂— | —CN | m.p. 108–112° C. |
| 1.11 | H | —CH(CH₃)— | —CN | m.p. 121–124° C. |
| 1.12 | H | —CH₂—CH₂— | =N—OH, —NH₂ | m.p. 186–189° C. |
| 1.13 | Cl | —CH(CH₃)— | —CN | m.p. 143–145° C. |

TABLE 1-continued

| No. | R | R' | Substituent | m.p. |
|---|---|---|---|---|
| 1.14 | H | -CH(CH$_3$)- | -C(=NOH)NH$_2$ | m.p. 191–194° C. (decomp.) |
| 1.15 | Cl | -CH(CH$_3$)- | -C(=NOH)NH$_2$ | m.p. 186–189° C. (decomp.) |
| 1.16 | H | -CH$_2$- | -C(NH$_2$)=N-O-C(=O)-C$_3$H$_5$-cycl. | m.p. 165–166° C. |
| 1.17 | H | -CH$_2$- | -C(NH$_2$)=N-O-C(=O)-C$_6$H$_4$-Cl(p) | m.p. 139–141° C. |
| 1.18 | Cl | -CH$_2$- | -C(NH$_2$)=N-O-C(=O)-CH$_3$ | m.p. 141–143° C. |
| 1.19 | Cl | -CH$_2$- | -C(NH$_2$)=N-O-C(=O)-OCH$_3$ | m.p. 148–149° C. |
| 1.20 | Cl | -CH$_2$- | -C(NH$_2$)=N-O-C(=O)-O-C$_2$H$_5$ | m.p. 139–140° C. |
| 1.21 | H | -CH$_2$- | -C(NH$_2$)=N-O-C(=O)-S-C$_5$H$_{11}$-n | m.p. 111–114° C. |
| 1.22 | H | -CH$_2$- | -C(NH$_2$)=N-O-C(=O)-CH=CH-CH$_3$ | m.p. 158–162° C. |
| 1.23 | H | -CH$_2$- | -C(NH$_2$)=N-O-C(=O)-NH-C$_2$H$_5$ | m.p. 123–125° C. |
| 1.24 | H | -CH$_2$- | -C(NH$_2$)=N-O-C(=O)-N(CH$_3$)(OCH$_3$) | m.p. 138–139° C. |

TABLE 1-continued

| No. | R | Linker | Structure | m.p. |
|---|---|---|---|---|
| 1.25 | H | $-CH_2-$ | acetamidoxime O-n-butyrate | m.p. 120–122° C. |
| 1.26 | Cl | $-CH_2-$ | acetamidoxime O-propionate | m.p. 157–158° C. (decomp.) |
| 1.27 | H | $-CH_2-$ | acetamidoxime O-(3-chloropropanoate) | m.p. 144–146° C. |
| 1.28 | H | $-CH_2-$ | acetamidoxime O-(2,3-dichloropropanoate) | m.p. 112–114° C. |
| 1.29 | Cl | $-CH_2-$ | acetamidoxime O-isobutyrate | m.p. 173–174° C. |
| 1.30 | H | $-CH_2-$ | acetamidoxime O-phenylcarbonate | m.p. 155–156° C. |
| 1.31 | H | $-CH_2-$ | acetamidoxime O-pivalate | m.p. 107–110.5° C. |
| 1.32 | H | $-CH_2-$ | acetamidoxime O-isovalerate | m.p. 124–126° C. |
| 1.33 | H | $-CH_2-$ | acetamidoxime O-(2-chlorophenyl)carbonate | m.p. 131–132° C. |
| 1.34 | H | $-CH_2-$ | acetamidoxime O-(sec-butoxyacetate) | m.p. 84–86° C. |

TABLE 1-continued
| | | | |
|---|---|---|---|
| 1.35 | H | —CH₂— | 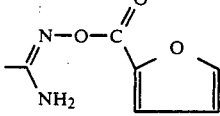 m.p. 168–169° C. |
| 1.36 | H | —CH₂— | 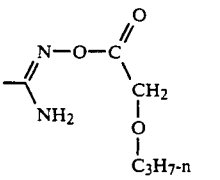 m.p. 101–103° C. |
| 1.37 | Cl | —CH₂— | 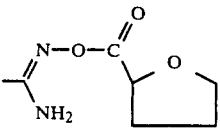 m.p. 156–157° C. (decomp.) |
| 1.38 | H | —CH₂— | 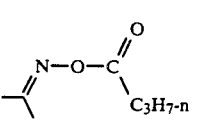 m.p. 82–85° C. |
| 1.39 | H | —CH₂— | 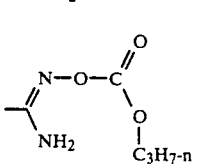 m.p. 144–147° C. |
| 1.40 | H | —CH₂— | 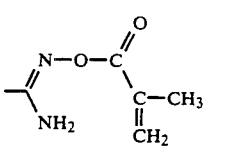 m.p. 128–130° C. |
| 1.41 | H | —CH₂— | 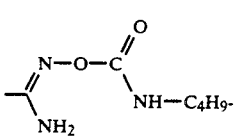 m.p. 104–107° C. |
| 1.42 | H | —CH₂— | 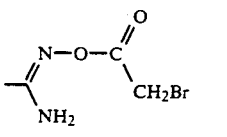 m.p. 132–134° C. |
| 1.43 | H | —CH₂— | 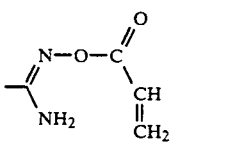 m.p. 138–140° C. |
| 1.44 | H | —CH₂— | 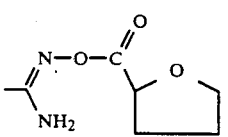 m.p. 129–131° C. |
| 1.45 | H | —CH₂— | 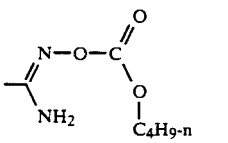 m.p. 121–123° C. |

TABLE 1-continued

| | | | |
|---|---|---|---|
| 1.46 | H | —CH₂— | [structure: amidoxime O-carbonate with –O–CH₂–CH=CH₂ (allyloxy)] | m.p. 123–125° C. |
| 1.47 | H | —CH₂— | [structure: amidoxime O-carbonate with –O–CH₂–CH₂Br] | m.p. 127–128° C. (decomp.) |
| 1.48 | Cl | —CH₂— | [structure: amidoxime O-carbonate with cyclopropyl (C₃H₅-cycl.)] | m.p. 173–175° C. |
| 1.49 | H | —CH₂— | [structure: amidoxime O-carbonate with –O–CH₂–C₆H₅ (benzyloxy)] | m.p. 135–137° C. |
| 1.50 | Cl | —CH₂— | [structure: amidoxime O-carbonate with 2-furyl] | m.p. 191–192° C. (decomp.) |
| 1.51 | H | —CH₂— | [structure: amidoxime with –S–C₂H₅ thiocarbonate] | m.p. 120–121° C. |
| 1.52 | H | —CH₂— | [structure: amidoxime O-carbonate with –CH₂–O–CH₃] | m.p. 118–120° C. |
| 1.53 | Cl | —CH₂— | [structure: amidoxime O-carbamate with –NH–(4-Cl-C₆H₄)] | m.p. 191–192° C. (decomp.) |
| 1.54 | H | —CH₂— | [structure: amidoxime O-carbonate with –CH₂–C₆H₅ (phenylacetate)] | m.p. 158–159° C. |

TABLE 1-continued
| 1.55 | H | —CH₂— | 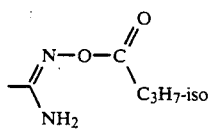 | m.p. 115–117.5° C. |
| --- | --- | --- | --- | --- |
| 1.56 | H | —CH₂— | 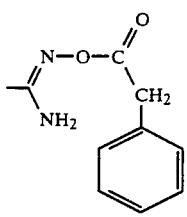 | m.p. 140–142° C. |
| 1.57 | H | —CH₂— | 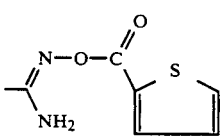 | m.p. 164–165° C. |
| 1.58 | H | —CH₂— | 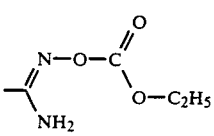 | m.p. 129–132° C. |
| 1.59 | H | —CH₂— | 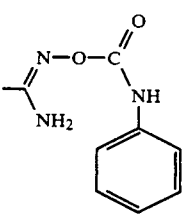 | m.p. 155–157.5° C. |
| 1.60 | H | —CH₂— | 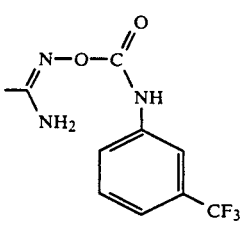 | m.p. 158–160° C. |
| 1.61 | Cl | —CH₂— | 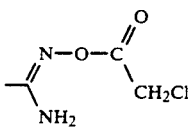 | m.p. 155–158° C. (decomp.) |
| 1.62 | H | —CH₂— | 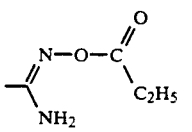 | m.p. 144–146° C. |
| 1.63 | H | —CH₂— | 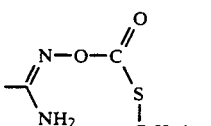 | m.p. 123–124° C. |

TABLE 1-continued

| | | | | |
|---|---|---|---|---|
| 1.64 | H | —CH₂— | 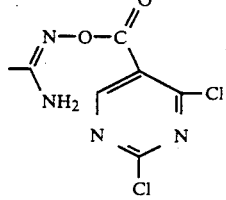 | m.p. 173–176° C. (decomp.) |
| 1.65 | H | —CH₂— | 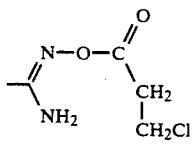 | m.p. 134–136° C. (decomp.) |
| 1.66 | H | —CH₂— | 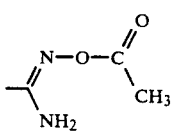 | m.p. 100–102° C. |
| 1.67 | H | —CH₂— | 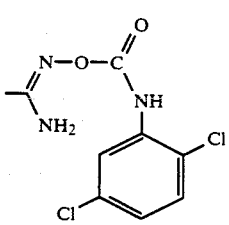 | m.p. 197–199° C. |
| 1.68 | H | —CH₂— | 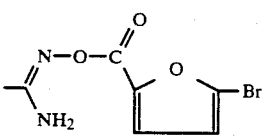 | m.p. 170–171° C. |
| 1.69 | H | —CH— $\|$ CH₃ | —COOCH₃ | m.p. 70–72° C. |
| 1.70 | H | —CH₂— | —COOH.H₂O | m.p. 184–185° C. |
| 1.71 | H | —CH₂— | —COOCH₂CH₂OCH₃ | m.p. 80–82° C. |
| 1.72 | H | —CH₂— | —COOCH₃ | m.p. 46.5–67.0° C. |
| 1.73 | H | —CH₂— | —COOC₂H₅.H₂O | m.p. 56–59° C. |
| 1.74 | H | —CH— $\|$ CH₃ | —CONH(CH₂)₃OC₂H₅ | m.p. 54–56° C. |
| 1.75 | H | —CH— $\|$ CH₃ | —CONHC₂H₅ | m.p. 86–88° C. |
| 1.76 | H | —CH₂— | —COOC₃H₇-n | m.p. 28–31° C. |
| 1.77 | H | —CH₂— | —COOC₃H₇-iso | $n_D^{23}$ = 1.5696 |
| 1.78 | H | —CH₂— | —CONHCH₃.H₂O | m.p. 74–81° C. |
| 1.79 | H | —CH₂— | 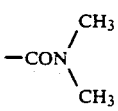 | m.p. 142–145° C. |
| 1.80 | H | —CH₂— | —CONHC₂H₅ | $n_D^{22.5}$ = 1.6002 |
| 1.81 | H | —CH— $\|$ CH₃ | —CONH(CH₂)₃OH | m.p. 120–122° C. |
| 1.82 | H | —CH₂— | —COOCH₂CH₂OC₂H₅ | $n_D^{24}$ = 1.5673 |

TABLE 1-continued

| | | | | |
|---|---|---|---|---|
| 1.83 | H | —CH(CH₃)— | —CONHCH₂—C₆H₅ | m.p. 88–90° C. |
| 1.84 | H | —CH₂— | —CONH(CH₂)₃CH₃ | m.p. 66–68° C. |
| 1.85 | H | —CH(CH₃)— | —CON(CH₃)(CH₂CH₂OH) | $n_D^{22} = 1.6054$ |
| 1.86 | H | —CH₂— | —CON(CH₃)(CH₂CH₂OH) | m.p. 146–149° C. |
| 1.87 | H | —CH₂— | —COOCH₂—(tetrahydrofuran-2-yl) | viscous mass |
| 1.88 | H | —CH(CH₃)— | —CONH(CH₂)₃CH₃·H₂O | m.p. 73–76° C. |
| 1.89 | H | —CH(CH₃)— | —CO—N(morpholino) | m.p. 120–121° C. |
| 1.90 | H | —CH(CH₃)— | —CON(CH₃)₂ | m.p. 105–111° C. |
| 1.91 | Cl | —CH₂— | —COOH | m.p. 232–233° C. |
| 1.92 | Cl | —CH₂— | —COOCH₂CH₂OCH₃ | m.p. 97–98° C. |
| 1.93 | Cl | —CH₂— | —COOCH₃ | m.p. 104–105.5° C. |
| 1.94 | Cl | —CH₂— | —COOC₂H₅ | m.p. 116–117° C. |
| 1.95 | Cl | —CH₂— | —COOC₃H₇-n | m.p. 108–109° C. |
| 1.96 | Cl | —CH₂— | —CON(CH₃)₂ | m.p. 135–136° C. |
| 1.97 | Cl | —CH₂— | —COOC₄H₉-tert | m.p. 63–69° C. |
| 1.98 | H | —CH₂— | —COOC₄H₉-tert | m.p. 68–70° C. |
| 1.99 | Cl | —CH₂— | —COOCH₂—C≡CH | m.p. 115–116° C. |
| 1.100 | Cl | —CH₂— | —COOC₃H₇-iso | m.p. 147–148° C. |
| 1.101 | Cl | —CH₂— | —COOCH₂CH₂OC₂H₅ | m.p. 102–104° C. |
| 1.102 | Cl | —CH₂— | —COOCH₂—C₆H₅ | m.p. 110–112° C. |
| 1.103 | Cl | —CH₂— | —COOCH₂—CH=CH₂ | m.p. 98–99° C. |
| 1.104 | Cl | —CH₂— | —COO(CH₂)₁₁CH₃ | m.p. 76–77° C. |
| 1.105 | Cl | —CH₂— | —COOC₄H₉-sec | m.p. 110–111° C. |
| 1.106 | H | —CH₂— | —COO(CH₂)₇CH₃ | $n_D^{24} = 1.5419$ |
| 1.107 | Cl | —CH₂— | —COOC₄H₉-n | m.p. 90.5–92° C. |
| 1.108 | H | —CH₂— | —COO(CH₂)₁₁CH₃ | $n_D^{23} = 1.5232$ |
| 1.109 | H | —CH₂— | —COOCH₂—CH=CH₂ | $n_D^{23} = 1.5885$ |
| 1.110 | Cl | —CH₂— | —COO(CH₂)₇CH₃ | m.p. 87–88° C. |
| 1.111 | H | —CH₂— | —COOC₄H₉-n | $n_D^{22} = 1.5642$ |
| 1.112 | H | —CH₂— | —COOC₄H₉-sec | red oil |
| 1.113 | Cl | —CH₂— | —COOCH₂CH₂Cl | m.p. 125–126° C. |
| 1.114 | H | —CH₂— | —COOCH₂—C₆H₅ | $n_D^{23.5} = 1.6099$ |

TABLE 1-continued

| | | | |
|---|---|---|---|
| 1.115 | Cl | —CH$_2$— | —COOCH$_2$—[tetrahydrofuran-2-yl] | m.p. 101–103° C. |
| 1.116 | Cl | —CH$_2$— | —COS(CH$_2$)$_7$CH$_3$ | m.p. 53–54° C. |
| 1.117 | H | —CH$_2$— | —COOCH$_2$CH$_2$Cl | m.p. 109–110° C. |
| 1.118 | H | —CH$_2$— | —COOC$_4$H$_9$-iso | $n_D^{22}$ = 1.5632 |
| 1.119 | H | —CH$_2$— | —COOCH(CH$_3$)CH$_2$CH$_2$CH$_3$ | $n_D^{22}$ = 1.5391 |
| 1.120 | H | —CH$_2$— | —COOCH(CH$_3$)(CH$_2$)$_5$CH$_3$ | $n_D^{22}$ = 1.5342 |
| 1.121 | H | —CH$_2$— | —CONH(CH$_2$)$_{11}$CH$_3$ | m.p. 56–61° C. |
| 1.122 | H | —CH$_2$— | —CONHCH$_2$CH$_2$—N(morpholino) | m.p. 94–99° C. |
| 1.123 | H | —CH$_2$— | —CONHCH$_2$CH$_2$CH$_2$OH | m.p. 138–139° C. |
| 1.124 | H | —CH$_2$— | —CONH—cyclohexyl(H) | m.p. 104–106° C. |
| 1.125 | H | —CH$_2$— | —CON(morpholino) | m.p. 99–103° C. |
| 1.126 | H | —CH$_2$— | —CONHCH$_2$CH$_2$N(C$_2$H$_5$)$_2$ | $n_D^{23}$ = 1.5686 |
| 1.127 | H | —CH$_2$— | —CON(CH$_2$CH$_2$OH)$_2$ | m.p. 144–146° C. |
| 1.128 | H | —CH$_2$— | —CONH(CH$_2$)$_3$N(CH$_3$)$_2$ | $n_D^{23}$ = 1.5766 |
| 1.129 | H | —CH$_2$— | —CON(CH$_3$)(C$_4$H$_9$-n) | $n_D^{22}$ = 1.5840 |
| 1.130 | H | —CH$_2$— | —CONHCH$_2$—phenyl · H$_2$O | m.p. 70.5–73.5° C. |
| 1.131 | H | —CH$_2$— | —CONHCH(CH$_2$OH)CH$_2$CH$_3$ | m.p. 150–151° C. |
| 1.132 | H | —CH$_2$— | —CON(C$_4$H$_9$-n)$_2$ · 2H$_2$O | m.p. 105–106° C. |

-continued

| No. | | | | |
|---|---|---|---|---|
| 1.133 | H | $-CH_2-$ | $-CONHCH_2CH_2-N\langle\text{piperidine}\rangle$ | $n_D^{26} = 1.5821$ |
| 1.134 | H | $-CH_2-$ | $-CONH(CH_2)_3N(CH_2CH_2OH)_2$ | m.p. 109–110° C. |
| 1.135 | H | $-CH_2-$ | $-CONHCH_2-CH=CH_2 \cdot H_2O$ | m.p. 71–75° C. |
| 1.136 | H | $-CH_2-$ | $-CONHCH_2-\langle\text{tetrahydrofuran-2-yl}\rangle \cdot H_2O$ | m.p. 57–58° C. |
| 1.137 | H | $-CH_2-$ | $-CONH(CH_2)_3OC_2H_5$ | m.p. 51–61° C. |
| 1.138 | H | $-CH_2-$ | $-CONHCH_2CH_2NHCH_2CH_2OH$ | m.p. 70–91° C. |
| 1.139 | Cl | $-CH_2-$ | $CONH(CH_2)_3OC_2H_5$ | m.p. 85–88° C. |
| 1.140 | Cl | $-CH_2-$ | $-CON(CH_3)(CH_2CH_2OH)$ | m.p. 187–189° C. |
| 1.141 | Cl | $-CH_2-$ | $-CON(CH_2CH_2OH)_2$ | m.p. 177–179° C. |
| 1.142 | Cl | $-CH_2-$ | $-CON\langle\text{morpholine}\rangle$ | m.p. 148–150° C. |
| 1.143 | Cl | $-CH_2-$ | $-CONHCH_2CH_2CH_2OH$ | m.p. 157–160° C. |
| 1.144 | Cl | $-CH_2-$ | $-CONHC_4H_9\text{-}n \cdot H_2O$ | m.p. 87–90° C. |
| 1.145 | Cl | $-CH_2-$ | $-CONHC_2H_5$ | m.p. 94–98° C. |
| 1.146 | Cl | $-CH_2-$ | $-CONHCH_2-C_6H_5 \cdot \tfrac{1}{2}H_2O$ | m.p. 146–149° C. |
| 1.147 | H | $-CH_2-$ | $-CONHNH_2 \cdot H_2O$ | m.p. 121–124° C. |
| 1.148 | H | $-CH_2-$ | $-COONa \cdot H_2O$ | m.p. 140–142° C. |
| 1.149 | H | $-CH_2-$ | $-COOK \cdot H_2O$ | m.p. >200° C. |
| 1.150 | H | $-CH_2-$ | $-COO^{\ominus} \ H\overset{\oplus}{N}(CH_3)_3$ | m.p. 176–178° C. |
| 1.151 | H | $-CH_2-$ | $-COO^{\ominus} \ H\overset{\oplus}{N}(CH_2CH_2OH)_3$ | m.p. 97–98° C. |
| 1.152 | Cl | $-CH_2-$ | $-COOK \cdot H_2O$ | m.p. >260° C. |
| 1.153 | Cl | $-CH_2-$ | $-COONa \cdot H_2O$ | m.p. >260° C. |
| 1.154 | H | $-CH_2-$ | $-COO^{\ominus} \ H\overset{\oplus}{N}(C_2H_5)_3$ | m.p. 255–257° C. (decomp.) |
| 1.155 | Cl | $-CH_2-$ | $-COO^{\ominus}\overset{\oplus}{H}N_4$ | m.p. 227–228° C. (decomp.) |
| 1.156 | Cl | $-CH_2-$ | $-COO^{\ominus} \ H\overset{\oplus}{N}(CH_2CH_2OH)_3$ | m.p. 132–156° C. (decomp.) |
| 1.157 | Cl | $-CH(CH_3)-$ | $-COO\text{-}(2,4\text{-dimethylphenyl})$ | m.p. 120–122° C. |
| 1.158 | Cl | $-CH_2-$ | $-COOCH(CH_3)(CH_2)_5CH_3$ | m.p. 65–67° C. |
| 1.159 | Cl | $-CH_2-$ | $-COOCH_2CH=CH-CH_3$ | m.p. 100–102° C. |

-continued

| | | | |
|---|---|---|---|
| 1.160 Cl | —CH$_2$— | —COOCH$_2$—C(CH$_3$)=CH$_2$ | m.p. 94–95° C. |
| 1.161 Cl | —CH$_2$— | —COOCH$_2$CH$_2$OC$_3$H$_7$-iso | m.p. 70–72° C. |
| 1.162 Cl | —CH$_2$— | —COOCH$_2$CH$_2$—O—C$_6$H$_5$ | m.p. 79–80.5° C. |
| 1.163 Cl | —CH(CH$_3$)— | —COOC$_3$H$_7$-iso | $n_D^{24}$ = 1.5642 |
| 1.164 Cl | —CH(CH$_3$)— | —COO(CH$_2$)$_7$CH$_3$ | $n_D^{23}$ = 1.5356 |
| 1.165 Cl | —CH(CH$_3$)— | —COOCH(CH$_3$)(CH$_2$)$_5$CH$_3$ | $n_D^{25}$ = 1.5370 |
| 1.166 Cl | —CH(CH$_3$)— | —COO(CH$_2$)$_{11}$CH$_3$ | m.p. 54–55° C. |
| 1.167 Cl | —CH(CH$_3$)— | —COOCH$_2$—C$_6$H$_5$ | m.p. 57–59° C. |
| 1.168 Cl | —CH(CH$_3$)— | —COOCH$_2$CH$_2$OC$_3$H$_7$-iso | $n_D^{32}$ = 1.5403 |
| 1.169 Cl | —CH(CH$_3$)— | —COOCH$_2$CH$_2$O—C$_6$H$_5$ | $n_D^{29}$ = 1.5962 |
| 1.170 Cl | —CH(CH$_3$)— | —COOCH$_2$CH=CH$_2$ | m.p. 40–41° C. |
| 1.171 Cl | —CH(CH$_3$)— | —COOCH$_2$CH=CH—CH$_3$ | m.p. 39–40° C. |
| 1.172 Cl | —CH(CH$_3$)— | —COOCH$_2$—C(CH$_3$)=CH$_2$ | m.p. 62–63° C. |
| 1.173 Cl | —CH(CH$_3$)— | —COO—cyclohexyl | $n_D^{30}$ = 1.5677 |
| 1.174 Cl | —CH$_2$— | —COO—C$_6$H$_5$ | m.p. 165–170° C. |
| 1.175 Cl | —CH$_2$— | —COO—C$_6$H$_4$—CH$_3$ | m.p. 143–145° C. |

-continued

| No. | X | A | Z | physical constant |
|---|---|---|---|---|
| 1.176 | Cl | —CH$_2$— | 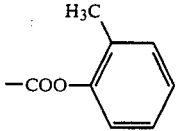 | m.p. 111–116° C. |
| 1.177 | Cl | —CH$_2$— | 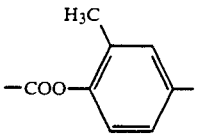 | m.p. 108–119° C. |
| 1.178 | Cl | —CH— <br> \|  <br> CH$_3$ | 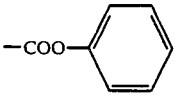 | m.p. 102–105° C. |

| No. | X | A + Z | physical constant |
|---|---|---|---|
| 1.179 | Cl | 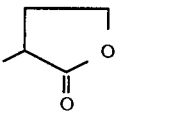 | m.p. 140–141.5° C. |

| No. | X | A | Z | physical constant |
|---|---|---|---|---|
| 1.180 | Cl | —CH$_2$— | —COOCHCH$_2$CH$_2$CH$_3$ <br>          \|  <br>          CH$_3$ | m.p. 65–70° C. |
| 1.181 | H | —CH$_2$— | —COOCH$_2$—CH(CH$_2$)$_2$CH$_3$ <br>                    \|  <br>                    CH$_3$ | n$_D^{22}$ = 1.5525 |
| 1.182 | Cl | —CH$_2$— | 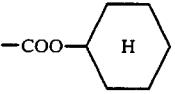 | m.p. 112–113° C. |
| 1.183 | Cl | —CH$_2$— | —COOCH$_2$CH—CH$_3$ <br>             \|  <br>             CH$_3$ | m.p. 113–114° C. |
| 1.184 | H | —CH$_2$— | —COO(CH$_2$)$_2$CHCH$_3$ <br>                \|  <br>                OCH$_3$ | n$_D^{22}$ = 1.5580 |
| 1.185 | H | —CH$_2$— | —COOCH$_2$CH$_2$OCH$_2$CH$_2$O(CH$_2$)$_3$CH$_3$ | n$_D^{22}$ = 1.5389 |
| 1.186 | H | —CH$_2$— | —COS(CH$_2$)$_3$CH$_3$ | n$_D^{23}$ = 1.6096 |
| 1.187 | H | —CH$_2$— | 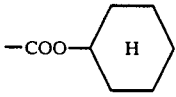 | n$_D^{23}$ = 1.5755 |
| 1.188 | H | —CH$_2$— | —COO(CH$_2$)$_4$CH$_3$ | n$_D^{23}$ = 1.5591 |
| 1.189 | H | —CH$_2$— | —COS(CH$_2$)$_7$CH$_3$ | n$_D^{22}$ = 1.5697 |
| 1.190 | Cl | —CH$_2$— | —COOCH$_2$—CH(CH$_2$)$_2$CH$_3$ <br>                    \|  <br>                    CH$_3$ | m.p. 74–75° C. |
| 1.191 | Cl | —CH$_2$— | —COS(CH$_2$)$_3$CH$_3$ | n$_D^{22}$ = 1.6076 |
| 1.192 | H | —CH$_2$— | —COOCH$_2$CH=CH—CH$_3$ | n$_D^{22}$ = 1.5833 |
| 1.193 | H | —CH$_2$— | —COOCH$_2$—CH—C$_2$H$_5$ <br>                \|  <br>                C$_2$H$_5$ | n$_D^{23}$ = 1.5530 |
| 1.194 | Cl | —CH$_2$— | —COOCH$_2$CH$_2$OCH$_2$CH$_2$O(CH$_2$)$_3$CH$_3$ | m.p. 39–41° C. |
| 1.195 | Cl | —CH$_2$— | —COO(CH$_2$)$_2$CHCH$_3$ <br>                \|  <br>                OCH$_3$ | m.p. 72–73° C. |
| 1.196 | Cl | —CH$_2$— | —COO(CH$_2$)$_4$CH$_3$ | m.p. 78–79° C. |

-continued

| No. | | | Property |
|---|---|---|---|
| 1.197 | Cl | —CH$_2$— —COOCH(C$_2$H$_5$)—(CH$_2$)$_2$CH$_3$ | m.p. 37–46° C. |
| 1.198 | H | —CH$_2$— —COOCH$_2$CH$_2$OC$_3$H$_7$-iso | n$_D^{22}$ = 1.5546 |
| 1.199 | Cl | —CH$_2$— —COO(CH$_2$)$_{13}$CH$_3$ | m.p. 75–76° C. |
| 1.200 | H | —CH$_2$— —COOCH(C$_2$H$_5$)—C$_2$H$_5$ | m.p. 47–50° C. |
| 1.201 | H | —CH$_2$— —COO-(2-methylcyclohexyl) | m.p. 29–31° C. |
| 1.202 | Cl | —CH$_2$— —COOCH$_2$—CH(C$_2$H$_5$)—C$_2$H$_5$ | m.p. 58–63° C. |
| 1.203 | H | —CH$_2$— —COOCH$_2$CH$_2$OCH$_2$CH$_2$OC$_2$H$_5$ | n$_D^{22}$ = 1.5489 |
| 1.204 | H | —CH$_2$— —COOCH$_2$CH$_2$O—C$_6$H$_5$ | m.p. 80–81° C. |
| 1.205 | Cl | —CH$_2$— —COOCH(C$_2$H$_5$)—C$_2$H$_5$ | m.p. 55–80° C. |
| 1.206 | H | —CH$_2$— —COOCH(CH$_3$)CH$_2$CH(CH$_3$)—CH$_3$ | n$_D^{22}$ = 1.5463 |
| 1.207 | H | —CH$_2$— —COO(CH$_2$)$_{13}$CH$_3$ | m.p. 35–36° C. |
| 1.208 | H | —CH$_2$— —COOCH$_2$CH$_2$O(CH$_2$)$_3$CH$_3$ | n$_D^{22}$ = 1.5495 |
| 1.209 | Cl | —CH$_2$— —COOCH$_2$CH$_2$OCH$_2$CH$_2$OC$_2$H$_5$ | m.p. 42–43° C. |
| 1.210 | H | —CH$_2$— —COOCH$_2$—CH(CH$_3$)—C$_2$H$_5$ | n$_D^{22}$ = 1.5566 |
| 1.211 | Cl | —CH$_2$— —COOCH(CH$_3$)CH$_2$CH(CH$_3$)—CH$_3$ | m.p. 63–64° C. |
| 1.212 | H | —CH$_2$— —COSCH(CH$_3$)—C$_2$H$_5$ | n$_D^{22}$ = 1.5973 |
| 1.213 | Cl | —CH$_2$— —COO-(2-methylcyclohexyl) | m.p. 98–101° C. |
| 1.214 | H | —CH$_2$— —COOC(CH$_3$)(C$_2$H$_5$)—C$_2$H$_5$ | n$_D^{22}$ = 1.5551 |
| 1.215 | H | —CH$_2$— —COOCH$_2$—C(CH$_3$)=CH$_2$ | n$_D^{22}$ = 1.5805 |
| 1.216 | H | —CH$_2$— —COOC(CH$_3$)(C$_2$H$_5$)—CH=CH$_2$ | n$_D^{22}$ = 1.5793 |
| 1.217 | H | —CH$_2$— —COOCH$_2$CH$_2$OCH$_2$CH$_2$OCH$_3$ | n$_D^{23}$ = 1.5560 |

-continued

| No. | R | R' | R'' | Phys. data |
|---|---|---|---|---|
| 1.218 | Cl | —CH₂— | —COOC(CH₃)(C₂H₅)C₂H₅ | $n_D^{22}$ = 1.5632 |
| 1.219 | Cl | —CH₂— | —COO(CH₂)₁₀CH₃ | m.p. 70–71° C. |
| 1.220 | Cl | —CH₂— | —COOCH₂—CH(CH₃)—C₂H₅ | m.p. 78–79° C. |
| 1.221 | H | —CH₂— | —COO—(cyclohexyl-H)—CH₃ | m.p. 40–42° C. |
| 1.222 | H | —CH₂— | —COO(CH₂)₆CH₃ | $n_D^{23}$ = 1.5469 |
| 1.223 | H | —CH₂— | —COOC(CH₃)(CH₃)C₂H₅ | $n_D^{22}$ = 1.5581 |
| 1.224 | Cl | —CH₂— | —COOCH₂CH₂O(CH₂)₃CH₃ | m.p. 69–70° C. |
| 1.225 | Cl | —CH₂— | —COSCH(CH₃)—C₂H₅ | m.p. 55–56° C. |
| 1.226 | Cl | —CH₂— | —COOC(CH₃)(CH₃)—CH=CH₂ | m.p. 83–87° C. |
| 1.227 | H | —CH₂— | —COSCH₃ | m.p. 41–44° C. |
| 1.228 | Cl | —CH₂— | —COOCH₂CH₂OCH₂CH₂OCH₃ | $n_D^{23}$ = 1.5633 |
| 1.229 | Cl | —CH₂— | —COSCH₃ | m.p. 89–91° C. |
| 1.230 | Cl | —CH₂— | —COOC(CH₃)(CH₃)C₂H₅ | m.p. 53–54° C. |
| 1.231 | H | —CH₂— | —COO(CH₂)₁₀CH₃ | $n_D^{23}$ = 1.5310 |
| 1.232 | Cl | —CH₂— | —COO(CH₂)₆CH₃ | m.p. 74–76° C. |
| 1.233 | H | —CH₂— | —COOCH(CH₃)—CH(CH₃)—CH₃ | $n_D^{23}$ = 1.5554 |
| 1.234 | Cl | —CH₂— | —COO—(cyclohexyl-H)—CH₃ | m.p. 103–105° C. |
| 1.235 | H | —CH₂— | —COSC(CH₃)(CH₃)CH₃ | $n_D^{23}$ = 1.5987 |
| 1.236 | Cl | —CH₂— | —COS(CH₂)₁₁CH₃ | m.p. 26–28° C. |
| 1.237 | Cl | —CH₂— | —COS(CH₂)₉CH₃ | m.p. 29–31° C. |
| 1.238 | Cl | —CH₂— | —COO(CH₂)₉CH₃ | m.p. 73–74° C. |
| 1.239 | H | —CH₂— | —COOCH(CH₃)(CH₂)₄CH₃ | $n_D^{23}$ = 1.5433 |
| 1.240 | Cl | —CH₂— | —COOCH(C₃H₇-n)—C≡CH | m.p. 81–82° C. |
| 1.241 | H | —CH₂— | —COOCH(C₅H₁₁-n)—CH=CH₂ | $n_D^{23}$ = 1.5472 |

| | | | -continued |
|---|---|---|---|
| 1.242 | Cl | $-CH_2-$ | $-COOCH(CH_3)-CH(CH_3)-CH_3$ | m.p. 70-74° C. |
| 1.243 | Cl | $-CH_2-$ | $-COSC(CH_3)_2-CH_3$ | $n_D^{22} = 1.5996$ |
| 1.244 | H | $-CH_2-$ | $-COOCH(CH_3)-C\equiv CH$ | $n_D^{23} = 1.5837$ |
| 1.245 | H | $-CH_2-$ | $-COS(CH_2)_{11}CH_3$ | $n_D^{23} = 1.5523$ |
| 1.246 | H | $-CH_2-$ | $-COOCH_2-C(CH_3)_3$ | $n_D^{22} = 1.5524$ |
| 1.247 | H | $-CH_2-$ | $-COSC_2H_5$ | $n_D^{23} = 1.6310$ |
| 1.248 | Cl | $-CH_2-$ | $-COOCH_2-C(CH_3)_3$ | m.p. 76-81° C. |
| 1.249 | Cl | $-CH_2-$ | $-COSC_3H_7\text{-n}$ | $n_D^{22} = 1.6136$ |
| 1.250 | H | $-CH_2-$ | $-COO(CH_2)_9CH_3$ | $n_D^{22} = 1.5308$ |
| 1.251 | Cl | $-CH_2-$ | $-COOCH(CH_3)(CH_2)_4CH_3$ | m.p. 65-67° C. |
| 1.252 | H | $-CH_2-$ | $-COO(CH_2)_2CH(CH_3)-CH_3$ | $n_D^{23} = 1.5568$ |
| 1.253 | H | $-CH_2-$ | $-COOCH(C_2H_5)(CH_2)_3CH_3$ | $n_D^{23} = 1.5454$ |
| 1.254 | Cl | $-CH_2-$ | $-COO(CH_2)_8CH_3$ | m.p. 78-79° C. |
| 1.255 | H | $-CH_2-$ | $-COSCH_2CH(CH_3)CH_3$ | $n_D^{23} = 1.6049$ |
| 1.256 | Cl | $-CH_2-$ | $-COSC_2H_5$ | m.p. 55-57° C. |
| 1.257 | H | $-CH_2-$ | $-COO(CH_2)_8CH_3$ | $n_D^{24} = 1.5436$ |
| 1.258 | Cl | $-CH_2-$ | $-COOCH_2-CH(C_2H_5)(CH_2)_3CH_3$ | m.p. 45-47° C. |
| 1.259 | Cl | $-CH_2-$ | $-COSCH_2CH(CH_3)-CH_3$ | $n_D^{23} = 1.6045$ |
| 1.260 | H | $-CH_2-$ | $-COS(CH_2)_9CH_3$ | $n_D^{23} = 1.5630$ |
| 1.261 | Cl | $-CH_2-$ | $-COO(CH_2)_2CH(CH_3)-CH_3$ | m.p. 72-74° C. |
| 1.262 | Cl | $-CH_2-$ | $-COOCH(C_2H_5)(CH_2)_3CH_3$ | $n_D^{22} = 1.5542$ |
| 1.263 | H | $-CH_2-$ | $-COO(CH_2)_5CH_3$ | $n_D^{22} = 1.5512$ |
| 1.264 | H | $-CH_2-$ | $-COOCH(C_3H_7\text{-n})(CH_2)_2CH_3$ | m.p. 48-50° C. |
| 1.265 | H | $-CH_2-$ | $-COS(CH_2)_4CH_3$ | $n_D^{22} = 1.5937$ |
| 1.266 | H | $-CH_2-$ | $-COSC_3H_7\text{-iso}$ | $n_D^{23} = 1.5821$ |
| 1.267 | H | $-CH_2-$ | $-COOCH_2CH(C_2H_5)-(CH_2)_3CH_3$ | $n_D^{22} = 1.5395$ |

-continued

| No. | | | | |
|---|---|---|---|---|
| 1.268 | Cl | —CH$_2$— | —COOCH(CH$_2$)$_2$CH$_3$ with C$_3$H$_7$-n | m.p. 55–57° C. |
| 1.269 | Cl | —CH$_2$— | —COS(CH$_2$)$_5$CH$_3$ | n$_D^{22}$ = 1.5882 |
| 1.270 | Cl | —CH$_2$— | —COS(CH$_2$)$_4$CH$_3$ | n$_D^{23}$ = 1.5990 |
| 1.271 | Cl | —CH$_2$— | —COO(CH$_2$)$_5$CH$_3$ | m.p. 71–72° C. |
| 1.272 | Cl | —CH$_2$— | —COSC$_3$H$_7$-iso | m.p. 62–64° C. |
| 1.273 | Cl | —CH$_2$— | —COOCH—CH$_2$CHC$_2$H$_5$ with C$_2$H$_5$, CH$_3$ | m.p. 25–29° C. |
| 1.274 | H | —CH$_2$— | —COOCH—C$_3$H$_7$-iso with C$_3$H$_7$-iso | n$_D^{22}$ = 1.5468 |
| 1.275 | H | —CH$_2$— | —COOCH—(CH$_2$)$_3$CH$_3$ with CH$_3$ | n$_D^{23}$ = 1.5531 |
| 1.276 | Cl | —CH$_2$— | —COOCH—CH=CH$_2$ with C$_5$H$_{11}$-n | n$_D^{23}$ = 1.5579 |
| 1.277 | H | —CH$_2$— | —COOCH—(CH$_2$)$_2$CH$_3$ with C$_2$H$_5$ | m.p. 42–44° C. |
| 1.278 | H | —CH$_2$— | —COSC$_3$H$_7$-n | n$_D^{22}$ = 1.6108 |
| 1.279 | Cl | —CH$_2$— | —COOCH—(CH$_2$)$_3$CH$_3$ with CH$_3$ | m.p. 68–71° C. |
| 1.280 | H | —CH$_2$— | —COOCHCH$_2$CHC$_2$H$_5$ with C$_2$H$_5$, CH$_3$ | n$_D^{23}$ = 1.5472 |
| 1.281 | Cl | —CH$_2$— | —COOCH—C$_3$H$_7$-iso with C$_3$H$_7$-iso | m.p. 88–89° C. |
| 1.282 | H | —CH$_2$— | —COS(CH$_2$)$_5$CH$_3$ | n$_D^{22}$ = 1.5804 |
| 1.283 | H | —CH$_2$— | —COO(CH$_2$)$_9$—CH=CH$_2$ | n$_D^{22}$ = 1.5386 |
| 1.284 | H | —CH$_2$— | —COOCH—C≡CH with C$_3$H$_7$-iso | n$_D^{22}$ = 1.5659 |
| 1.285 | Cl | —CH$_2$— | —COOCH—C≡CH with CH$_3$ | m.p. 97–100° C. |
| 1.286 | H | —CH$_2$— | —COOC—C≡CH with CH$_3$, C$_2$H$_5$ | n$_D^{22}$ = 1.5688 |
| 1.287 | Cl | —CH$_2$— | —COO(CH$_2$)$_9$—CH=CH$_2$ | m.p. 66–67° C. |
| 1.288 | Cl | —CH$_2$— | —COO—C—C≡CH with CH$_3$, CH$_3$ | m.p. 76–81° C. |
| 1.289 | H | —CH$_2$— | —COO—C—C≡CH with CH$_3$, CH$_3$ | n$_D^{23}$ = 1.5740 |
| 1.290 | Cl | —CH$_2$— | —COO—C—C≡CH with CH$_3$, C$_2$H$_5$ | m.p. 78–79° C. |

-continued
| | | | |
|---|---|---|---|
| 1.291 | Cl | —CH₂— | 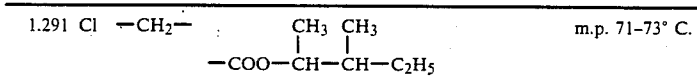 m.p. 71–73° C. |
| 1.292 | Cl | 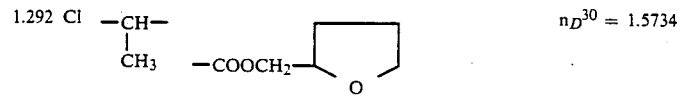 | $n_D^{30}$ = 1.5734 |
| 1.293 | Cl | —CH₂— | —COOCH₂COOC₄H₉-n  m.p. 52–54° C. |
| 1.294 | Cl | —CH₂— | 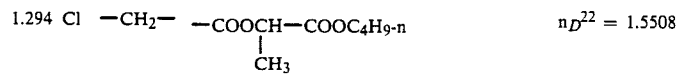 $n_D^{22}$ = 1.5508 |
| 1.295 | Cl | —CH₂— | 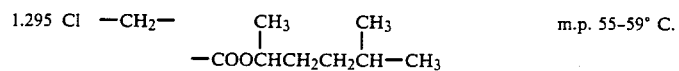 m.p. 55–59° C. |
| 1.296 | Cl | —CH₂— | 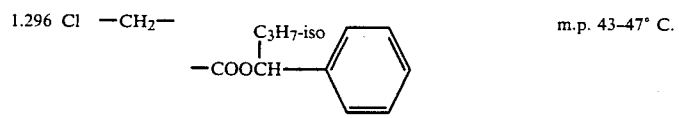 m.p. 43–47° C. |
| 1.297 | Cl | —CH₂— | 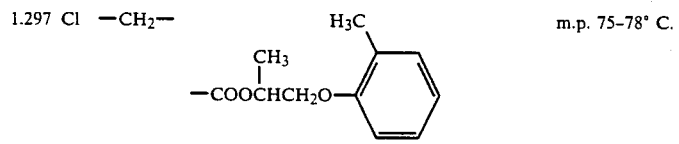 m.p. 75–78° C. |
| 1.298 | Cl | —CH₂— | 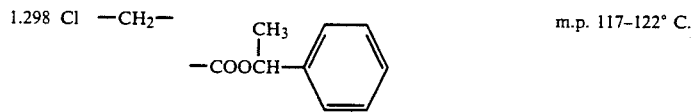 m.p. 117–122° C. |
| 1.299 | Cl | —CH₂— | 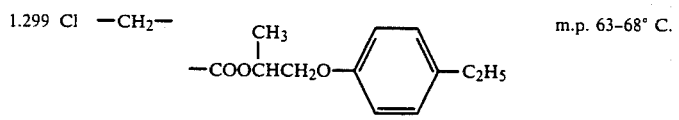 m.p. 63–68° C. |
| 1.300 | Cl | —CH₂— | 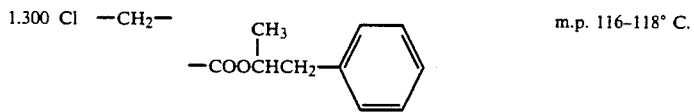 m.p. 116–118° C. |
| 1.301 | Cl | —CH₂— | 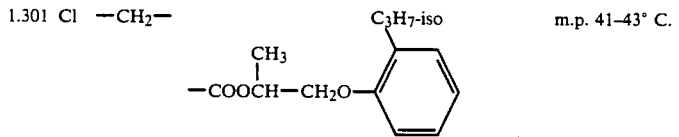 m.p. 41–43° C. |
| 1.302 | Cl | —CH₂— | 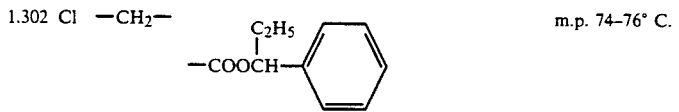 m.p. 74–76° C. |
| 1.303 | Cl | —CH₂— | 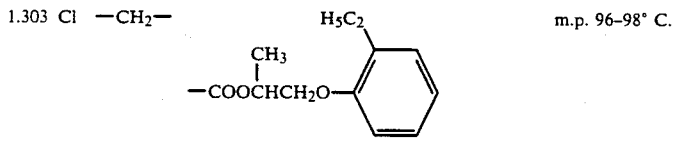 m.p. 96–98° C. |
| 1.304 | Cl | —CH₂— | 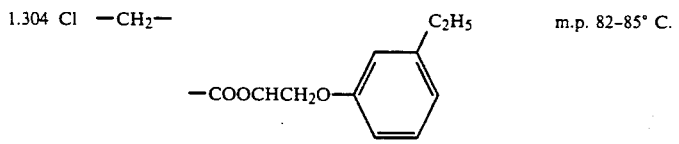 m.p. 82–85° C. |

-continued

| | | | |
|---|---|---|---|
| 1.305 | Cl | —CH$_2$—  —COOCHCH$_2$O—⟨phenyl⟩ with CH$_3$ | m.p. 42–44° C. |
| 1.306 | Cl | —CH$_2$—  —COOCHCH$_2$CH$_2$—⟨phenyl⟩ with CH$_3$ | m.p. 78–79° C. |
| 1.307 | Cl | —CH$_2$—  —COOCHCH$_2$O—⟨phenyl⟩ with CH$_3$ and CH$_3$ | m.p. 58–61° C. |
| 1.308 | Cl | —CH$_2$—  —COOCHCH$_2$O—⟨phenyl⟩—C$_3$H$_7$-iso, with CH$_3$ | m.p. 35–38° C. |
| 1.309 | Cl | —CH$_2$—  —COOCHCH$_2$O—⟨phenyl⟩—CH$_3$, with CH$_3$ | m.p. 82–84° C. |

The invention relates also to a method for the selective control of weeds in crops of useful plants, which comprises treating the useful plants, the seeds or seedlings thereof or the cultivation area thereof with a herbicidally effective amount of the N-benzoyl-N-(3-chloro-4-fluorophenyl)-alanine derivative of formula I and a herbicide-antagonistically effective amount of a quinoline derivative of formula II, simultaneously or independently of one another.

Cultivated plants that can be protected by the quinoline derivatives of formula II against the damaging effects of the above-mentioned herbicides are especially those that are important in the food and textile sectors, for example sugar cane and, especially, sorghum, maize, rice and other species of cereal (wheat, rye, barley, oats).

The weeds to be controlled may be both monocotyledonous and dicotyledonous weeds.

There come into consideration as cultivated plants or parts of those plants, for example, those mentioned above. Cultivation areas will be understood as meaning areas of land in which the cultivated plants are already growing or in which the seed of those cultivated plants has already been sown, and also ground intended for growing those cultivated plants.

A safener or antidote of formula II can, depending on the purpose of use, be used to pre-treat the seed of the cultivated plant (dressing the seeds or seedlings) or can be introduced into the soil before or after sowing has taken place. It can, however, also be applied by itself or together with the herbicide before or after the emergence of the plants. The treatment of the plant or the seed with the antidote can therefore in principle take place independently of the time of application of the phytotoxic chemical. The plant can, however, also be treated by applying the phytotoxic chemical and the safener simultaneously (tank mixture). Preemergence treatment includes both treatment of the cultivation area before sowing (ppi=pre plant incorporation) and treatment of cultivation areas in which seed has been sown but in which the plants have not yet grown.

The rate of application of the antidote relative to that of the herbicide depends largely on the mode of application. In the case of field treatment, which is effected either using a tank mixture with a combination of antidote and herbicide or by separate application of antidote and herbicide, the ratio of antidote and herbicide is generally from 1:100 to 10:1, preferably from 1:20 to 1:1, and especially 1:1. In contrast, in the case of seed dressing, much lower amounts of antidote are required relative to the rate of application of herbicide per hectare of cultivation area.

In the case of field treatment, 0.001 to 5.0 kg antidote/ha, preferably 0.01 to 0.5 kg antidote/ha, will usually be applied.

In the case of seed-dressing, 0.01 to 10 g antidote/kg seed, preferably 0.05 to 2 g antidote/kg seed, will generally be applied. If the antidote is applied in liquid form shortly before sowing by seed soaking, then it is advantageous to use antidote solutions that contain the active ingredient in a concentration of 1 to 10,000, preferably 100 to 1,000 ppm.

For the purpose of application, the compounds of formula II or combinations of compounds of formula II with the herbicides to be antagonised are advantageously used together with the adjuvants conventionally employed in the art of formulation, and are therefore formulated in known manner, e.g. into emulsifiable concentrates, coatable pastes, directly sprayable or dilutable solutions, dilute emulsions, wettable powders, soluble powders, dusts, granulates, and also encapsulations in e.g. polymer substances. As with the nature of the compositions to be used, the methods of application, such as spraying, atomising, dusting, scattering, coating or pouring, are chosen in accordance with the intended objectives and the prevailing circumstances.

The formulations, i.e. the compositions, preparations or mixtures containing the compound (active ingredient) of formula II, or a combination of the compound of formula II with the herbicide to be antagonised, and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are, for example, calcite or sand. In addition, a great number of pregranulated materials of inorganic or organic nature can be used, e.g. especially dolomite or pulverised plant residues.

Depending on the nature of the compound of formula II to be formulated and, where appropriate, also on the nature of the herbicide to be antagonised, suitable surface-active compounds are nonionic, cationic and/or anionic surfactants having good emulsifying, dispersing and wetting properties. The term "surfactants" will also be understood as comprising mixtures of surfactants.

Both so-called water-soluble soaps and also water-soluble synthetic surface-active compounds are suitable anionic surfactants.

Suitable soaps are the alkali metal salts, alkaline earth metal salts or unsubstituted or substituted ammonium salts of higher fatty acids ($C_{10}$-$C_{22}$), e.g. the sodium or potassium salts of oleic or stearic acid or of natural fatty acid mixtures which can be obtained e.g. from coconut oil or tallow oil. Fatty acid methyltaurin salts may also be mentioned as surfactants.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde.

Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, saturated or unsaturated fatty acids and alkylphenols, said derivatives contains 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit. Representative examples of non-ionic surfactants are nonylphenolpolyethoxyethanols, castor oil polyglycol ethers, polypropylene/polyethylene oxide adducts, tributylphenoxy-polyethoxyethanol, polyethylene glycol and octylphenoxy-polyethoxyethanol.

Fatty acid esters of polyoxyethylene sorbitan, e.g. polyoxyethylene sorbitan trioleate, are also suitable.

Cationic surfactants are preferably quaternary ammonium salts which contain, as N-substituent, at least one $C_8$-$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyl-trimethyl-ammonium chloride or benzyldi(2-chloroethyl)ethylammonium bromide.

The surfactants customarily employed in the art of formulation are described e.g. in the following publications:

"McCutcheon's Detergents and Emulsifiers Annual" MC Publishing Corp., Ridgewood, N.J., 1981. Stache, H., "Tensid-Taschenbuch", Carl Hanser Verlag Munich/Vienna 1981.

The agrochemical compositions usually contain 0.1 to 99% by weight, preferably 0.1 to 95% by weight, of a compound of formula I or a mixture of antidote and herbicide, 1 to 99.9% by weight, preferably 5 to 99.8% by weight, of a solid or liquid adjuvant and 0 to 25% by weight, preferably 0.1 to 25% by weight, of a surfactant.

Whereas commercial products are preferably formulated as concentrates, the end user will normally employ dilute formulations.

The compositions may also contain further ingredients such as stabilisers, antifoams, viscosity regulators, binders, tackifiers as well as fertilisers or other active ingredients for obtaining special effects.

Various methods and techniques are suitable for using compounds of formula II or compositions containing them for protecting cultivated plants against the damaging effects of herbicides of formula I. The following are examples thereof:

i) Seed dressing a) Dressing the seeds with a wettable powder formulation of a compound of formula II by shaking in a vessel until even distribution is obtained on the surface of the seeds (dry dressing). Approximately 1 to 500 g of compound of formula II (4 g to 2 kg of wettable powder) are used per 100 kg of seed.

b) Dressing the seeds with an emulsifiable concentrate of a compound of formula II according to the procedure of method a) (wet dressing).

c) Dressing by immersing the seed in a mixture containing 100 to 1000 ppm of compound of formula II for 1 to 72 hours and, if desired, subsequently drying the seeds (immersion dressing).

Dressing the seed or treating the germinated seedling are naturally the preferred methods of application since the active ingredient treatment is directed entirely to the target crop. Normally 1 to 1000 g of antidote, preferably 5 to 250 g of antidote, are used per 100 kg of seed, although it is possible, depending on the methodology which also permits the addition of other active ingredients or micronutrients, to deviate above or below the indicated limit concentrations (repeat dressings).

ii) Application from a tank mixture

A liquid formulation of a mixture of antidote and herbicide (ratio of the one to the other from 10:1 to 1:100) is used, the rate of application of herbicide being 0.01 to 5.0 kg per hectare. A tank mixture of this type is applied before or after sowing.

iii) Application to the seed furrow

The antidote is introduced in the form of an emulsifiable concentrate, wettable powder or granulate into the open, sown seed furrow and then, after covering the seed furrow, the herbicide is applied preemergence in the normal manner.

iv) Controlled release of active ingredient

A compound of formula II, in solution, is absorbed onto mineral granulate carriers or polymerised granulates (urea/formaldehyde) and allowed to dry. If desired, a coating may be applied (coated granulates) that allows the active ingredient to be released in controlled amounts over a specific period of time.

Formulation Examples for liquid active ingredients of formula II or mixtures thereof with a herbicide of the formula I (throughout, percentages are by weight)

| 1. Emulsifiable concentrates | (a) | (b) | (c) |
|---|---|---|---|
| compound or mixture | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexanone | — | 15% | 20% |
| xylene mixture | 65% | 25% | 20% |

Emulsions of any desired concentration can be produced from such concentrates by dilution with water.

| 2. Solutions | (a) | (b) | (c) | (d) |
|---|---|---|---|---|
| compound or mixture | 80% | 10% | 5% | 95% |
| ethylene glycol monomethyl ether | 20% | — | — | — |
| polyethylene glycol (mol. wt. 400) | — | 70% | — | — |
| N-methyl-2-pyrrolidone | — | 20% | — | — |
| epoxidised coconut oil | — | — | 1% | 5% |
| petroleum fraction (boiling range 169–190° C.) | — | — | 94% | — |

These solutions are suitable for application in the form of micro-drops.

| 3. Granulates | (a) | (b) |
|---|---|---|
| compound or mixture | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 4. Dusts | (a) | (b) |
|---|---|---|
| compound or mixture | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

Formulation Examples for solid active ingredients of formula II or mixtures thereof with a herbicide of the formula I (throughout, percentages are by weight)

| 5. Wettable powders | (a) | (b) | (c) |
|---|---|---|---|
| compound or mixture | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenolpolyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| 6. Emulsifiable concentrates | |
|---|---|
| compound or mixture | 10% |
| octylphenol polyethylene glycol ether (4–5 moles of ethylene oxide) | 3% |
| calcium dodecylbenzenesulfonate | 3% |
| castor oil polyglycol ether (35 moles of ethylene oxide) | 4% |
| cyclohexanone | 30% |
| xylene mixture | 50% |

Emulsions of any required concentration can be obtained from this concentrate by dilution with water.

| 7. Dusts | (a) | (b) |
|---|---|---|
| compound or mixture | 5% | 8% |
| talcum | 95% | — |
| kaolin | — | 92% |

Ready-for-use dusts are obtained by mixing the active ingredient with the carriers, and grinding the mixture in a suitable mill.

| 8. Extruder granulates | |
|---|---|
| compound or mixture | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a steam of air.

| 9. Coated granulates | |
|---|---|
| compound or mixture | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granulates are obtained in this manner.

| 10. Suspension concentrates | |
|---|---|
| compound or mixture | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

Biological Examples

The ability of the compounds of formula II to protect cultivated plants from the phytotoxic action of strong herbicides can be seen from the following example.

In order to investigate the safening action, seeds of barley (variety: Harrington and Bonanza) and of the weed grass Avena fatua are grown in soil in pots measuring 11 cm in diameter. The plants are cultivated in a greenhouse under appropriate temperature and light conditions. The plants are watered and fertilised as required.

The safener substance is applied postemergence at a rate of 200/100/50 g/ha in the form of a tank mixture with the herbicide at a rate of application of 800 and 600 g/ha and with a rate of application of water of 550 liters/hectare.

In order to determine the safening action (protective action) the general damage (phytotox) to the plants is assessed 17 days after application (0% phytotox=no damage, as treated control plant, 100% phytotox=total damage). The percentage protective action indicated in the Table is obtained from the difference between the phytotox of the herbicide treatment alone and that of the combination of herbicide+safener. The results are summarised below. The herbicide used is N-benzoyl-N-(3-chloro-4-fluorophenyl)-DL-alanine (Flamiprop racemate) and the safener used is 2-(5-chloroquinolin-8-yloxy)-acetic acid (1-methylhexyl) ester Compound 1.251.

| Herbicide rate of application | Safener rate of application | Protective action with | | |
|---|---|---|---|---|
| | | barley "Harrington" | barley "Bonanza" | Avena fatua |
| 800 g/ha | + 200 g/ha | 50% | 55% | 5% |
| 800 g/ha | + 100 g/ha | 40% | 45% | 5% |
| 800 g/ha | + 50 g/ha | 40% | 45% | 5% |
| 600 g/ha | + 200 g/ha | 40% | 35% | 5% |
| 600 g/ha | + 100 g/ha | 35% | 40% | 5% |
| 600 g/ha | + 50 g/ha | 40% | 40% | 5% |

Since the protective action in the case of barley is 7 to 11 times stronger than in the case of the weed grass, it is possible to control Avena fatua (wild oat) successfully in barley crops using this mixture.

What is claimed is:

1. A composition for the selective control of weeds in crops of useful plants comprising
   a) a herbicidally effective amount of a herbicide of formula I

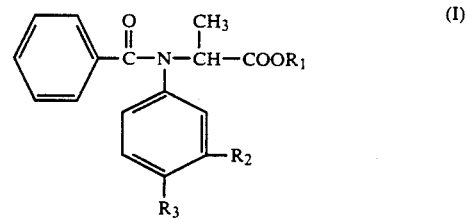

wherein
$R_1$ is hydrogen or $C_1$-$C_4$alkyl and each of $R_2$ and $R_3$, independently of the other, is chlorine or fluorine, or an enantiomer of said herbicide, and
   b) a safening-effective, amount of a safener compound of formula II

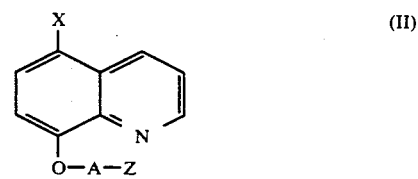

wherein X is hydrogen or halogen,
A is one of the groups —$CH_2$—, —$CH_2CH_2$— and —$CH(CH_3)$—, and Z is $COOR^{12}$ wherein $R^{12}$ is a $C_{1-7}$ alkyl group together with an inert carrier.

2. A composition according to claim 1, wherein the said herbicide is selected from the group consisting of
N-benzoyl-N-(3-chloro-4-fluorophenyl)-DL-alanine,
N-benzoyl-N-(3-chloro-4-fluorophenyl)-DL-alanine methyl ester,
N-benzoyl-N-(3-chloro-4-fluorophenyl)-DL-alanine ethyl ester,
N-benzoyl-N-(3-chloro-4-fluorophenyl)-D-alanine,
N-benzoyl-N-(3-chloro-4-fluorophenyl)-D-alanine methyl ester,
N-benzoyl-N-(3-chloro-4-fluorophenyl)-D-alanine isopropyl ester,
N-benzoyl-N-(3-chloro-4-fluorophenyl)-L-alanine and
N-benzoyl-N-(3-chloro-4-fluorophenyl)-L-alanine methyl ester.

3. A composition according to claim 1 wherein the said herbicide is N-benzoyl-N-(3-chloro-4-fluorophenyl)-DL-alanine methyl ester.

4. A composition according to claim 1, wherein the said herbicide is the (R)enantiomer of N-benzoyl-N-(3-chloro-4-fluorophenyl)-D-alanine.

5. A composition according to claim 1, wherein the said safener compound is selected from the group consisting of
2-quinolin-8-yloxy-acetic acid isopropyl ester,
2-(5-chloroquinolin-8-yloxy)-acetic acid n-butyl ester,
2-quinolin-8-yloxy-acetic acid sec.-butyl ester,
2-(5-chloroquinolin-8-yloxy)-acetic acid (1-methylbutyl)-ester,
2-(5-chloroquinolin-8-yloxy)-acetic acid sec.-butyl ester,
2-(5-chloroquinolin-8-yloxy)-acetic acid (2-methylpentyl)-ester,
2-(5-chloroquinolin-8-yloxy)-acetic acid (1-ethylbutyl)-ester,
2-(5-chloroquinolin-8-yloxy)-acetic acid (2-ethylbutyl)-ester,
2-(5-chloroquinolin-8-yloxy)-acetic acid (1-methylisopentyl)-ester,
2-(5-chloroquinolin-8-yloxy)-acetic acid (2-methylbutyl)-ester,
2-(5-chloroquinolin-8-yloxy)-acetic acid n-heptyl ester,
2-(5-chloroquinolin-8-yloxy)-acetic acid (1-methylisobutyl)-ester,
2-(5-chloroquinolin-8-yloxy)-acetic acid neopentyl ester,
2-(5-chloroquinolin-8-yloxy)-acetic acid (1-methylhexyl)-ester,
2-(5-chloroquinolin-8-yloxy)-acetic acid isopentyl ester,
2-(5-chloroquinolin-8-yloxy)-acetic acid (1-ethylpentyl)-ester,
2-(5-chloroquinolin-8-yloxy)-acetic acid (1-propylbutyl)-ester,
2-(5-chloroquinolin-8-yloxy)-acetic acid n-hexyl ester,
2-(5-chloroquinolin-8-yloxy)-acetic acid (1-methylpenyl)-ester and 6. A composition according to patent claim 1, wherein the said herbicide is N-benzoyl-N-(3-chloro-4-fluorophenyl)-DL-alanine and the said safener compound is 2-(5-chloroquinolin-8-yloxy)-acetic acid-n-pentyl ester.

7. A composition according to claim 1, wherein the said herbicide is N-benzoyl-N-(3-chloro-4-fluorophenyl)-DL-alanine and the said safener compound is 2-(5-chloroquinolin-8-yloxy)-acetic acid (1-methylhexyl) ester.

8. A method for the selective control of weeds and grasses in crops of useful plants, which comprises treating the crops, the seeds thereof or the cultivation area thereof with a herbicidally effective amount of a herbicide of formula I according to claim 1 and a safening-effective amount of a safener compound of formula II according to claim 1, simultaneously or independently of one another.

9. A method for the selective control of weeds and grasses in crops of useful plants, which comprises treating the crops, the seeds thereof or the cultivation area thereof with a herbicidally effective amount of a herbicide of formula I

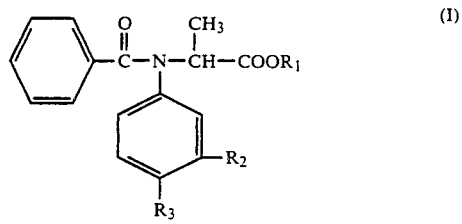

wherein
$R_1$ is hydrogen or $C_1$–$C_4$alkyl and each of $R_2$ and $R_3$, independently of the other, is chlorine or fluorine, or an enantiomer of said herbicide, and a safening-effective amount of a safener compound of claim 5, simultaneously or independently of one another.

10. A method according to claim 8 wherein the herbicide is N-benzoyl-N-(3-chloro-4-fluorophenyl)-DL-alanine.

11. A method according to claim 8, which comprises treating crops of cultivated plants or cultivation areas for cultivated plants with 0.25 to 2 kg/ha of a herbicide of formula I and 0.01 to 0.5 g/ha of a safener compound of formula II.

12. A method according to claim 8, which comprises treating seeds of the cultivated plant with 0.01 to 10 g/kg seeds of a safener compound of formula II.

* * * * *